(12) United States Patent
Rousso et al.

(10) Patent No.: US 9,233,075 B2
(45) Date of Patent: Jan. 12, 2016

(54) SATIETY

(75) Inventors: Benny Rousso, Rishon-LeZion (IL); Shlomo Ben-Haim, London (GB)

(73) Assignee: MetaCure Limited, Hamilton (BM)

( * ) Notice: Subject to any disclaimer, the term of this patent is extended or adjusted under 35 U.S.C. 154(b) by 1639 days.

(21) Appl. No.: 11/990,211

(22) PCT Filed: Aug. 9, 2006

(86) PCT No.: PCT/IB2006/052752
§ 371 (c)(1),
(2), (4) Date: Feb. 8, 2008

(87) PCT Pub. No.: WO2007/017842
PCT Pub. Date: Feb. 15, 2007

(65) Prior Publication Data
US 2009/0098198 A1    Apr. 16, 2009

Related U.S. Application Data (60) Provisional application No. 60/706,621, filed on Aug. 9, 2005.

(51) Int. Cl.
*A61K 9/48* (2006.01)
*A61F 5/00* (2006.01)

(52) U.S. Cl.
CPC ............. *A61K 9/4808* (2013.01); *A61F 5/0036* (2013.01)

(58) Field of Classification Search
None
See application file for complete search history.

(56) References Cited

U.S. PATENT DOCUMENTS

| | | | | |
|---|---|---|---|---|
| 3,385,715 A * | 5/1968 | Ishler et al. | | 426/274 |
| 3,600,825 A * | 8/1971 | Pearce | | 434/403 |
| 4,683,141 A * | 7/1987 | Lewis et al. | | 426/639 |
| 5,603,950 A * | 2/1997 | Ratjen et al. | | 424/451 |
| 6,571,127 B1 | 5/2003 | Ben-Haim et al. | | |
| 7,006,871 B1 | 2/2006 | Darvish et al. | | |
| 2002/0161414 A1 | 10/2002 | Flesler et al. | | |
| 2003/0055464 A1 | 3/2003 | Darvish et al. | | |
| 2003/0055467 A1 | 3/2003 | Ben-Haim et al. | | |
| 2003/0072804 A1 | 4/2003 | Hird et al. | | |
| 2003/0091610 A1 | 5/2003 | Hird et al. | | |
| 2003/0208242 A1 | 11/2003 | Harel et al. | | |
| 2004/0044376 A1 | 3/2004 | Flesler et al. | | |
| 2004/0059393 A1 | 3/2004 | Policker et al. | | |
| 2004/0147816 A1 | 7/2004 | Policker et al. | | |
| 2004/0249421 A1 | 12/2004 | Harel et al. | | |
| 2006/0074459 A1 | 4/2006 | Flesler et al. | | |
| 2006/0085045 A1 | 4/2006 | Harel et al. | | |
| 2006/0184207 A1 | 8/2006 | Darvisii et al. | | |
| 2007/0027493 A1 | 2/2007 | Ben-Haim et al. | | |
| 2007/0051849 A1 | 3/2007 | Watts et al. | | |
| 2007/0060812 A1 | 3/2007 | Harel et al. | | |
| 2007/0060971 A1 | 3/2007 | Glasberg et al. | | |
| 2007/0092446 A1 | 4/2007 | Haddad et al. | | |
| 2007/0156177 A1 | 7/2007 | Harel et al. | | |
| 2007/0179556 A1 | 8/2007 | Ben Haim et al. | | |
| 2007/0185540 A1 | 8/2007 | Ben-Haim et al. | | |
| 2007/0299320 A1 | 12/2007 | Policker et al. | | |
| 2008/0058889 A1 | 3/2008 | Ben-Haim et al. | | |
| 2008/0058891 A1 | 3/2008 | Ben-Haim et al. | | |
| 2008/0065168 A1 | 3/2008 | Bitton et al. | | |
| 2008/0178684 A1 | 7/2008 | Spehr | | |
| 2009/0062893 A1 | 3/2009 | Spehr | | |
| 2009/0088816 A1 | 4/2009 | Harel et al. | | |
| 2009/0118797 A1 | 5/2009 | Kliger et al. | | |
| 2009/0131993 A1 | 5/2009 | Rousso et al. | | |
| 2009/0204063 A1 | 8/2009 | Policker et al. | | |
| 2009/0281449 A1 | 11/2009 | Thrower et al. | | |
| 2010/0228105 A1 | 9/2010 | Policker et al. | | |
| 2010/0305468 A1 | 12/2010 | Policker et al. | | |
| 2010/0324644 A1 | 12/2010 | Levi et al. | | |

FOREIGN PATENT DOCUMENTS

| | | |
|---|---|---|
| DE | 10259508 A1 * | 7/2004 |
| WO | WO 99/03533 | 1/1999 |
| WO | WO 00/53257 | 9/2000 |
| WO | WO 01/10375 | 2/2001 |
| WO | WO 01/66183 | 9/2001 |
| WO | WO 01/91854 | 12/2001 |
| WO | WO 02/053093 | 7/2002 |
| WO | WO 02/082968 | 10/2002 |
| WO | WO 03/045493 | 6/2003 |
| WO | WO 2004002241 A1 * | 1/2004 |
| WO | WO 2004/021858 | 3/2004 |
| WO | WO 2004/112563 | 12/2004 |
| WO | WO 2004/112883 | 12/2004 |
| WO | WO 2005/007232 | 1/2005 |
| WO | WO 2005/023081 | 3/2005 |

(Continued)

OTHER PUBLICATIONS

Raghuveer et al. Two-Point, Timesaving Method for Measurement of Gastric Emptying with Diagnostic Accuracy Comparable to That of the Conventional Mehod, Radiology 1999; 213:599-602.*

(Continued)

*Primary Examiner* — Michael G Hartley
*Assistant Examiner* — Nabila Ebrahim (57) ABSTRACT

A capsule for suppressing appetite, comprising:
a) a shell which dissolves in the stomach; and
b) a plurality of elements inside the shell, which elements expand inside the stomach, after the shell dissolves, to form a connected mass with an envelope volume greater than the total volume of the elements, and at least 3 times the volume of the capsule.

34 Claims, 5 Drawing Sheets

(56) References Cited

FOREIGN PATENT DOCUMENTS

| WO | WO 2005/087310 | 9/2005 |
| WO | WO 2006/018851 | 2/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

Tropac Inc, Special Capsules, Capsule Machinery Soluble containes, Capsule Size Chart, 2000.*

Translation of reference CN1744831A published Mar. 8, 2006 equivalent to DE10259508.*

International Preliminary Report From the International Bureau Dated Dec. 11, 2008 Re. Application No. PCT/IB2006/052752.

International Search Report Dated Jan. 3, 2008 From the International Searching Authority Re. Application No. PCT/TB2006/052752.

Written Opinion Dated Jan. 3, 2008 From the International Searching Authority Re. Application No. PCT/1B2006/052752.

* cited by examiner

SATIETY

RELATED APPLICATIONS

This Application is a National Phase of PCT Patent Application No. PCT/IB2006/052752 having International Filing Date of Aug. 9, 2006, which claims the benefit under 35 USC 119(e) of U.S. Provisional Patent Application No. 60/706,621 filed on Aug. 9, 2005. The contents of the above Applications are all incorporated herein by reference.

FIELD OF THE INVENTION

The field of the invention relates to inducing a sensation of satiety, for example, in order to treat obesity.

BACKGROUND OF THE INVENTION

Obesity is becoming increasingly widespread in the developed world, and the medical dangers of obesity are well known. Non-invasive treatment, by diet and exercise, is difficult for many patients to maintain. Surgical treatments include surgically reducing the usable volume of the stomach. Such surgery is effective but expensive, and, like any major surgery, has risks, especially for patients whose obesity has caused other health problems. Less extreme methods include wiring the jaws closed, and planting an expandable balloon in the stomach, either surgically or endoscopically. But these procedures can be uncomfortable, and also carry risks.

U.S. Pat. No. 5,032,415, to Battista, describes pills containing a swelling material, such as a compressed mass of cellulose fibers, which are swallowed and swell in the stomach, suppressing appetite. U.S. Pat. No. 6,271,278, to Park et al, describes superabsorbent material which is encapsulated in gelatin, and swallowed, swelling in the stomach once the gelatin dissolves.

U.S. Pat. No. 6,548,083, to Wong et al, and U.S. Pat. No. 6,488,962, to Berner et al, describe material which is swallowed and swells in the stomach, not for suppressing appetite, but in order to release drugs into the stomach gradually, over a period as long as 24 hours.

U.S. Pat. No. 6,627,206, to Lloyd, describes small magnetic cubes or tetrahedrons which are swallowed, a few at a time, in capsules. After the capsules dissolve in the stomach, the magnets self-assemble into a space-filling mass, which suppresses appetite.

U.S. Pat. No. 4,812,315, to Tarabishi, describes a balloon, folded in accordion fashion, and swallowed in a capsule. The balloon contains sodium bicarbonate, and once the capsule dissolves in the stomach, the balloon absorbs hydrochloric acid which reacts with the sodium bicarbonate, producing carbon dioxide which expands the balloon, suppressing appetite.

U.S. Pat. No. 4,607,618, to Angelchik, describes a hollow, semi-rigid device, which is collapsed and inserted into the stomach through an endoscopic feeding tube. In the stomach, the device spontaneously recovers its original shape, expanding, and suppresses appetite. Similar devices, in some cases inserted into the stomach directly through the esophagus, are described in U.S. Pat. No. 5,868,141, to Ellias, U.S. Pat. No. 4,648,383, U.S. Pat. No. 5,306,300, and U.S. Pat. No. 6,755,869.

U.S. Pat. No. 6,740,121 describes a stent, made of a bioabsorbable material, which is placed in the duodenum, limiting the uptake of food passing through it, until it degrades and passes from the body.

All of the devices described above have the potential disadvantage that they remain in the stomach for a long time, much longer than food normally remains in the stomach, and they can block the pylorus, or, if partially broken up, could potentially block the intestines. In some of these devices, there is also the potential danger that they could expand (or swell, for amorphous materials) prematurely in the esophagus, if the capsules dissolve before they reach the stomach for some reason.

As described in http://www.medid.com/bips_features.html, Medical ID Products produces x-ray opaque Barium Impregnated Polyethylene Spheres (BIPS) to help diagnose blockages and motility problems in the stomachs and intestines of cats and dogs. The spheres are packed in gelatin capsules which are swallowed whole and dissolve in the animal's stomach, or the loose spheres are mixed in with food which is fed to the animal.

All of the above patents and publications are incorporated herein by reference.

SUMMARY OF THE INVENTION

An aspect of some embodiments of the invention relates to a capsule to suppress appetite, adapted to be swallowed, comprising a plurality of shaped elements contained inside a shell. In an exemplary embodiment of the invention, when the shell dissolves in the stomach, the elements expand to a volume sufficient to suppress or reduce appetite, optionally expanding by a factor of 10 or more in volume. In an exemplary embodiment of the invention, the elements include hollow portions, for example, more than 50% of the envelope volume of an element may be void(s). In an exemplary embodiment of the invention, the elements clump together to form a mass. The envelope volume of the mass is optionally greater than the total volume of the individual elements. The mass optionally remains in the stomach for not too much longer than food normally remains in the stomach.

Optionally, while the shape of the mass may not be determinable ahead of time, the shape of some or all of the elements, is optionally predetermined.

In some embodiments of the invention, the elements comprise a material which swells in the stomach, for example, when it absorbs fluid in the stomach. Optionally, the material comprises a compressed food material which is already approved for human consumption, either in natural form or freeze-dried, such as freeze-dried carrot. Such food materials naturally break up and leave the stomach in approximately one to six hours, like other foods, or, in some cases, shorter or longer times.

In some embodiments of the invention, the elements are arranged in a mechanical structure which rearranges itself to have a larger volume, for example when it is released from confining forces exerted on it by the shell of the capsule. These embodiments have a potential advantage that the contents of the capsule may not expand if the shell accidentally disintegrates when it is still in the esophagus, since the confining force of the esophagus will prevent the geometric structure from rearranging itself. Alternatively or additionally, the rearrangement of the mechanical structure is at least partly caused by the elements absorbing fluid in the stomach. Optionally, the elements are made of a metal or plastic material which is not digested or degrades slowly. Optionally, the element comprises at least two parts of non-degrading or slowly degrading material attached by a part of degrading material, for example a joint made of a gum material.

In some embodiments of the invention, the expansion of the elements is due partly to expansion of the material of each element, caused by absorbing fluid, and partly to the rearrangement of the mechanical structure, caused by release from confining forces.

An aspect of some embodiments of the invention relates to a device that expands inside the stomach and is configured to collapse or otherwise stop exerting a satiating effect after a relatively short time, such as less than 10 hours, less than 6 hours, less than 3 hours or less than 1 hour. In an exemplary embodiment of the invention, some or all of the device is at least partially digested in the stomach, causing it to collapse.

An aspect of some embodiments of the invention relates to a device for taking up a volume of a predefined geometry in the stomach and formed of a food material. In an exemplary embodiment of the invention, the device is made of a fibrous vegetable.

An aspect of some embodiments of the invention relates to a method of expanding structures in the stomach in which the structure is formed of materials that both expand mechanically and expand due to swelling or other chemical interaction with stomach contents.

An aspect of some embodiments of the invention relates to a method of compressing vegetable material while retaining at least some elasticity thereof. In an exemplary embodiment of the invention, freeze-dried carrots, kohlrabi, or other vegetables are prepared in a way that makes them very elastic, so that they can be compressed to only a small fraction of their original volume before freeze-drying, for example 10%. The carrots or other vegetables are freeze-dried, optionally without prior cooking, or only slight cooking, until their water content is very low, for example less than 5% by weight, or less than 3%, and they may become brittle. Optionally, cooking is avoided to maintain elastic properties. Optionally, they are then allowed to absorb moisture for several hours in an environment where the relative humidity is greater than about 40%, but lower than 63% (i.e. water activity between 0.4 and 0.63) to avoid bacterial growth. Optionally, the water content reaches between 6% and 10% by weight, depending on the relative humidity used, and the vegetable become elastic and compressible. When released from compression they expand in volume, and they optionally expand further when they are placed in water. They may return to their original volume before freeze-drying or close to their original volume, for example by substantially regaining their original elastic properties, and/or by absorbing water.

There is thus provided, in accordance with an exemplary embodiment of the invention, a capsule for suppressing appetite, comprising:
 a) a shell which dissolves in the stomach; and
 b) a plurality of elements inside the shell, which elements expand inside the stomach, after the shell dissolves, to form a connected mass with an envelope volume greater than the total volume of the elements, and at least 3 times the volume of the capsule.

Optionally, the envelope volume is at least 5 times the volume of the capsule.

Optionally, the envelope volume is at least 10 times the volume of the capsule.

Optionally, the envelope volume is at least 20 times the volume of the capsule.

Optionally, the elements consist of material substantially all of which leaves the stomach of a normal person in less than 12 hours.

Optionally, substantially all of the material leaves the stomach in less than 9 hours.

Optionally, substantially all of the material leaves the stomach in less than 6 hours.

In an embodiment of the invention, the elements individually expand when they absorb fluid inside the stomach.

Optionally, the elements comprise a food material approved for human consumption.

Optionally, the food material comprises a freeze-dried vegetable.

Optionally, the material comprises between 6% and 10% water by weight.

Alternatively or additionally, the elements comprise an inert non-food material.

In an embodiment of the invention, the elements comprise a mechanical structure which is in a collapsed state when it is inside the shell, and which expands to a less collapsed state when it is released from the shell.

Optionally, the expansion of the mechanical structure is due at least partly to the removal of constraining forces exerted on the mechanical structure by the shell.

Alternatively or additionally, the expansion of the mechanical structure is at least partly triggered by exposure to water.

Optionally, the expansion of the mechanical structure is due at least partly to the absorption of fluid, which makes the mechanical structure more rigid.

Optionally, the expansion of the mechanical structure is due at least partly to the absorption of fluid which makes the individual elements expand.

Optionally, the mechanical structure corresponds to an array of polyhedrons, with each element corresponding to an edge of one or more of the polyhedrons.

There is further provided, in accordance with an exemplary embodiment of the invention, a method of inducing satiety in a patient, comprising feeding the patient one or more capsules according to an embodiment of the invention.

There is further provided, in accordance with an embodiment of the invention, a method of manufacture of elastic freeze-dried vegetable material, the method comprising:
 a) preparing freeze-dried vegetable material with a moisture content less than 5%; and
 b) humidifying the freeze-dried vegetable material until it has a water content at least 6% by weight, thereby making the material elastic.

There is further provided, in accordance with an exemplary embodiment of the invention, a method of manufacturing capsules of expandable material for inducing satiety, comprising:
 a) forming edible material into one or more shapes; and
 b) compressing the shapes and putting them in a capsule.

Optionally, the edible material comprises freeze-dried vegetable material prepared according to an embodiment of the invention.

BRIEF DESCRIPTION OF THE DRAWINGS

Exemplary non-limiting embodiments of the invention are described in the following sections with reference to the drawings. The drawings are not necessarily to scale, and same reference numbers are generally used for same or related features that are shown in different drawings.

DETAILED DESCRIPTION OF EXEMPLARY EMBODIMENTS

Figure 1A:
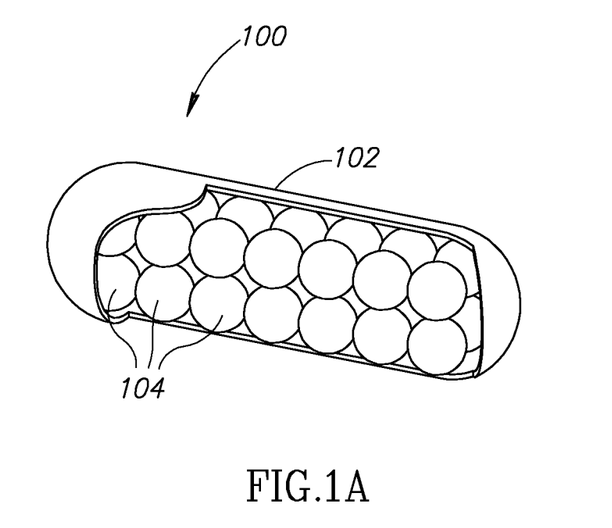
FIGS. 1A-1C schematically show a sequence of perspective views of expanding material released from a capsule, according to an exemplary embodiment of the invention.

FIG. 1A shows a cutaway view of a capsule 100, comprising a shell 102 containing compressed elements 104 of expandable material, for example freeze-dried carrot or other vegetable material, or cellulose sponge. Elements 104 may be packed into shell 102 in various manners, for example, being arranged in a 2×2×7 cubic array. The shell is, for example, a standard 00 size gelatin capsule shell, transparent or opaque, and each element 104 is optionally a sphere 3 mm in diameter. Alternatively, each element is about 2 mm in diameter, or 1 mm, or 0.5 mm or less, or about 5 mm, or about 10 mm or more, and the number of elements is accordingly greater than or less than 28, if the shell has the same dimensions, or the shell is smaller or greater in size. Alternatively, the elements are arranged in any other kind of array instead of a cubic array, or are not arranged in a regular array at all. Arranging the elements in an array potentially allows more efficient filling of the volume of the capsule with the material. If the shell is transparent, then arranging the elements in an array may also make the capsule more attractive to customers. The arrangement may depend on the shape of the elements. The elements need not all be the same shape.

As shown, the elements are spheres, all of substantially the same size. Alternatively, they are cubes, or flat plates, or rods, or star-shaped, or hook-shaped, or any other shape, or they are not all the same shape, or not all the same size. Optionally, the elements have holes in them, and the holes take up space when the elements are expanded in the stomach, but the holes are collapsed, taking up essentially no space, when the elements are compressed inside the shell. Optionally, the elements are ringed-shaped, and two or more of the rings are linked together. When the elements are compressed, the rings lie nearly flat, but when they are released from compression, the rings are oriented at random angles to each other, and take up more space.

Optionally, the shell protects the esophagus from sharp edges of the elements.

Using spheres has the potential advantage that the packing efficiency does not depend on the orientation of the elements. Using cubes, or flat plates, or another shape which can form a space-filling array, has the potential advantage that the elements can be packed into the capsule with greater fill efficiency than spheres can, if the elements are aligned properly. However, if the elements are very compressible, then they may be packed into the capsule with high fill efficiency even if they are spheres, or cubes that are not aligned carefully, or rods, or irregular in shape. Using star-shaped or hook-shaped elements has the potential advantage that the elements may link or lock together more easily in the stomach, to form a bulk mass, with empty space between them, especially in the presence of other food in the stomach. But the elements may still be folded up compactly when they are inside the shell. Making the elements all the same shape and size has the potential advantage that the packing efficiency does not depend on which element is located where, and the relative size of the elements and the capsule can be chosen so that the elements can be packed into the capsule with relatively high efficiency.

Optionally, the elements are coated with a sticky coating which causes them to remain stuck together, even after the shell dissolves, or the surface of the elements has a high coefficient of friction which prevents the elements from easily sliding past each other, so that they tend to form a bulk mass with empty space between them when they are expanded in the stomach. An advantage of having the elements remain stuck together is that the envelope volume of the array is greater than the total volume of the individual elements. The envelope volume may be what determines the effect on appetite. Optionally, the spaces between (and/or within) the elements are too small for other food in the stomach to easily enter into. Optionally, capsule 100, or another capsule taken with capsule 100, contains thickening agents which are released into the stomach, at least locally, when the capsule dissolves, making the nearby food thicker and less able to penetrate into the spaces between the elements. Alternatively or additionally, the thickening agent makes the material of elements 104 more solid, or stickier, so they form a bulk in the stomach.

Figure 1B:
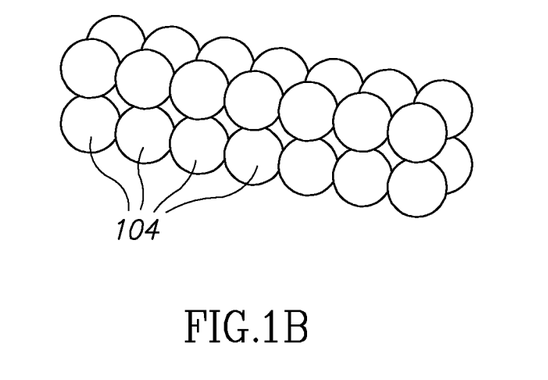

FIG. 1B shows the elements 104, in the stomach, after the shell, for example a gelatin capsule shell, has dissolved due to digestive enzymes and/or hydrochloric acid in the stomach. The elements are still the same size, since they have not yet absorbed fluid from the stomach. Tests show that a 00 size gelatin capsule dissolves in 37° C. water in about 5 minutes, and elements 104, if they are made of freeze-dried carrot with about 6% to 10% water, expand to their original volume, or at least to more than 70% of their original volume, in about another 5 to 10 minutes, if their original diameter was 8 to 12 mm. Optionally, as the shell dissolves, the elements expand due to mechanical reasons (e.g., having been elastically compressed in side the capsule). Optionally, the absorption of water triggers elastic expansion of one or more elements.

Figure 1C:
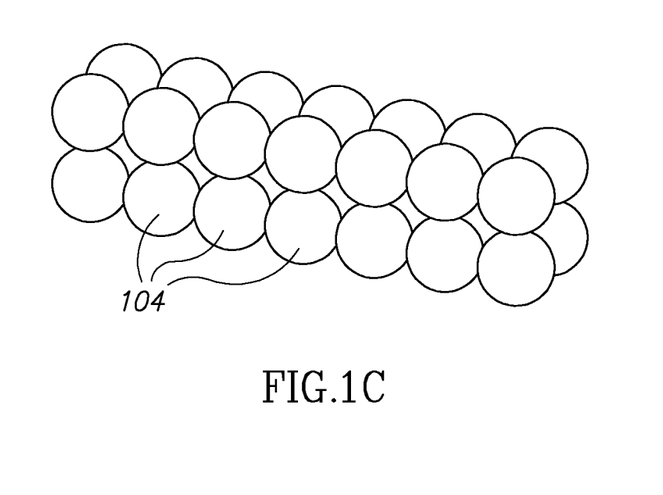

FIG. 1C shows the elements 104 after they were in contact with fluid in the stomach, causing the material to expand, for example due to absorption of water, or due to water triggering their expansion by increasing their elasticity. For example, freeze-dried carrot can expand by a factor of about 10 in volume when it is released from compression and it absorbs water at body temperature. The array of elements 104 is now about 10 cc or more in volume, enough to significantly suppress appetite, particularly if more than one such capsule is swallowed. Other expansion factors may be provided, for example, depending on the shape of the elements, sizes of voids and elastic properties of the elements, for example, a factor of 4, 6 or 8 or a factor higher than 10, for example, 12, 15, 20, 30 or more. For example, for a cuboid element made of 12 stick elements, each one with a cross-section of X mm$^2$, the compressed volume is 12XY, where Y is the dimension of the stick element, while the expanded volume can be large as Y^3. For a 10 mm cuboid element made of 1 mm$^2$ sticks, compressed volume can be (depending on the packing efficiency and ignoring the increased palatability provided by the dehydration of the element) 12*1*10=120 mm$^3$. The expanded volume (envelope) can be 10*10*10=1000 mm$^3$. If, for example, dehydration and compression affords another ratio of 4 of compressibility and packing efficiency is only 50%, the total expansion ratio will be about 1:16. Non-food materials, such as metal, may be stronger and use thinner dimensions and thus provide greater compressibility. In an exemplary embodiment of the invention, a single capsule generate a volume envelope of between 3 cc and 50 cc or more, for example, 5 cc, 10 cc, 20 cc, 30 cc, 40 cc or intermediate or greater values. Optionally, several capsules are swallowed at a time. It should be noted that some distortion of the element by the stomach may be allowed. This may assist in preventing damage to the stomach. Optionally, the resilience of the elements is chosen to have a desired effect on a feeling of fullness, for example, providing some resistance to compression by the stomach.

Elements 104 are optionally made of a material which is digested and leaves the stomach in a time not very much longer than the time that food remains in the stomach. For example, substantially all of the material leaves the stomach in less than 12 hours, or in less than 9 hours, or in less than 6 hours. Optionally, element 104 is an approved food material, such as freeze-dried carrot, as noted above, or a standard material approved for drugs. Using a material which leaves the stomach relatively quickly, particularly an approved food material, has the potential advantage that the material is not likely to cause blockage of the pylorus or the intestine. Alternatively or additionally, elements 104 are made of a material that dissolves in gastric juices, or that is bio-absorbent, even if it is not a food material. Alternatively or additionally, elements 104 are made of an inert bio-compatible material, such as silicone, Teflon, NiTi, titanium, or stainless steel, and pass along the digestive system without interacting with the body, except mechanically.

Making elements 104 out of carrots, or other vegetables such as kohlrabi, has the potential advantage that they can maintain their mechanical structure and elasticity after drying, with only small amounts of water present, for example 6% to 10% by weight. Fruits such as oranges may also be used, but since their structure is produced by fluid contained in small membranes, their structure may tend to collapse unless they retain a relatively high percentage of water. It may be desirable to select source materials in which an elastic structure not depending on water is used, for example, a fibrous or matrix-like structure.

Optionally, an absorbing material such as a gel or dough is used for elements 104. Optionally, a material such as a dough includes pores containing a carbonate, such as sodium bicarbonate or calcium carbonate, which produces carbon dioxide when it comes in contact with acid in the stomach, or a material is used which produces another gas that is safe. Optionally, the dough is of a consistency such that the pores allow some fluid from the stomach to enter, but the pores keep the resulting gas largely trapped, making the material expand.

Optionally, elements 104 comprise chopped loofah, for example compressed particles of loofah about 3 mm in diameter which expand to more than 5 times their compressed volume.

Optionally, capsule 100 includes drugs which contribute to weight loss by accelerating emptying of the stomach, before carbohydrates can be fully absorbed, or by inhibiting emptying of the stomach to keep the subject feeling full, or by inhibiting enzymes such as amylase, to prevent metabolism of starch, or lipase, to prevent metabolism of fats.

Optionally, instead of enclosing elements 104 in capsule 100, elements 104 are mixed in with food. This approach may be particularly useful if the material of elements 104 expands not so much due to releasing it from mechanical compression, but primarily due to absorbing fluid, or generating trapped gas. Optionally, materials that expand from mechanical compression are used encapsulated in small shells or trapped in the matrix of a relatively hard food, such as a cracker. If elements 104 are mixed in directly with food, then it may be advantageous for them to be formed in shapes that do not have sharp corners and edges, such as spheres, or cubes with rounded edges. Optionally, the elements are made flat to withstand some chewing action.

In an exemplary embodiment of the invention, elements 104 are mixed in with a drink, for example to form a suspension and/or to ease their being swallowed.

Optionally, the elements are coated with a material that does not dissolve in the drink, but that does dissolve in gastric juices, due to the acid for example. If elements 104 make up 5% or 10% of the volume of the food or drink, then they may expand up to 50% or 100% of the volume once they are inside the stomach.

Figure 2A:
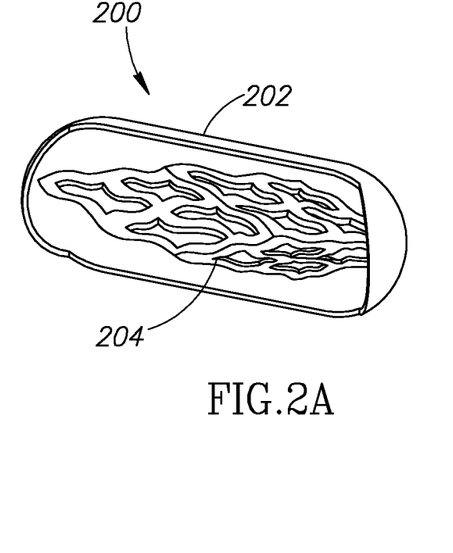
FIGS. 2A-2D schematically show a sequence of perspective views of expanding material released from a capsule, according to another exemplary embodiment of the invention.
Figure 2B:
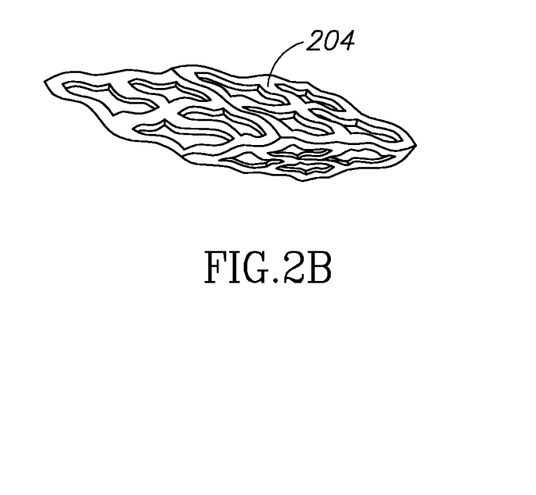
Figures 2C, 2D:
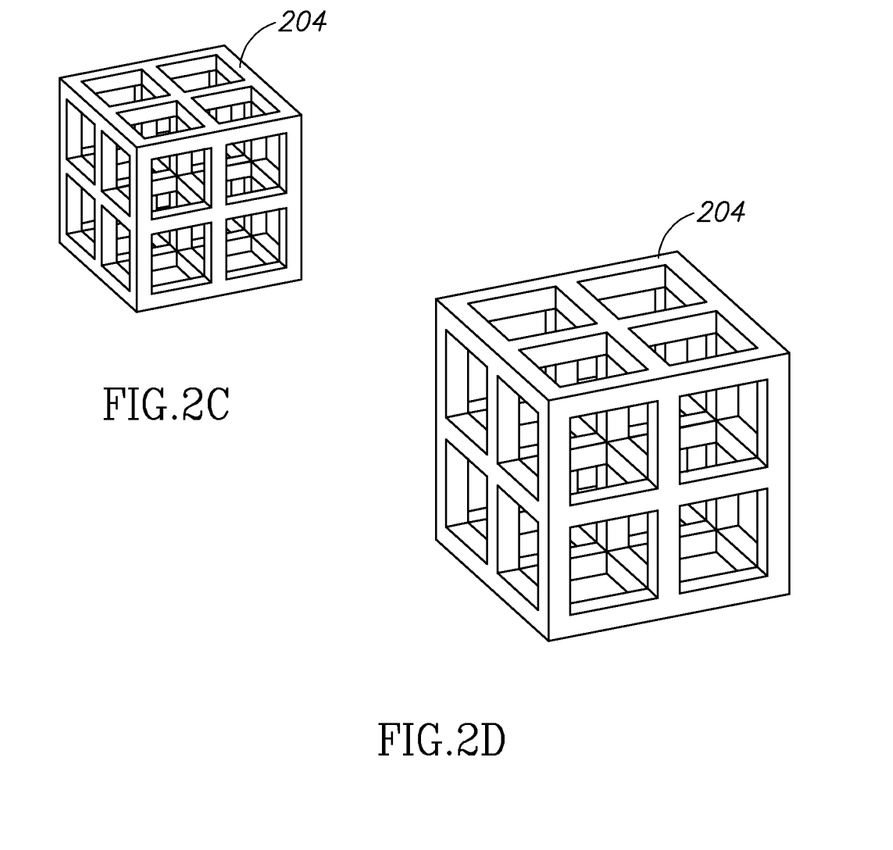

FIG. 2A shows a capsule 200 comprising a shell 202 containing a collapsed mechanical structure 204, according to an embodiment of the invention. Structure 204 is optionally made of any of the materials mentioned above for elements 104, although it may be advantageous to use a stiffer material in structure 204. Structure 204 comprises, for example, straight elements, each consisting of material surrounding the edge of a cube in an array of cubes, with material missing from the interiors of the cubes and from the centers of their faces. Although structure 204 is shown as a 2×2×2 array of cubes, it is optionally a single cube, or an array with any other number of cubes in each direction. When the material is dehydrated, for example by freeze-drying, structure 204 can be collapsed along a diagonal of the array, without breaking, and can be surrounded by shell 202, which keeps structure 204 in its collapsed state. After capsule 200 is swallowed, the shell dissolves, leaving collapsed structure 204, as shown in FIG. 2B. With shell 202 no longer restraining structure 204, structure 204 recovers its original cubic shape, as shown in FIG. 2C. Optionally, the recovery of collapsed structure 204 to its original cubic shape is assisted by, or depends on, the straight elements absorbing fluid from the stomach, which may make the material more rigid for example. Optionally, structure 204 also expands, as a result of absorbing fluid from the stomach, either while it recovers its original shape, or after it recovers its original shape, so that it becomes a larger cubic array, as shown in FIG. 2D. Structure 204 in FIG. 2D has a substantially larger envelope volume than capsule 200, because structure 204 has recovered its original shape and/or because the individual straight elements have expanded. As in FIG. 1C, it is the envelope volume that optionally primarily determines how well structure 204 suppresses appetite, for example, if the internal spaces in the cubic array are too small for other food to enter easily or if the stomach contacts the structure when contracting.

Alternatively, structure 204 comprises a different space-filling mechanical structure, for example an array of polyhedrons other than cubes, or an irregular structure. The array of cubes shown in FIGS. 2A-2D has the potential advantage that it can easily be made, by starting with a cube of material, and removing a square array of cores parallel to each of the principal axes. This method of manufacture may be used for other shapes as well.

Optionally, the straight elements of structure 204 are more rigid than the joints. For example, the straight elements can be thinner near their ends, where they join other straight elements, and thicker in their central regions. Optionally, the joints are shaped to reduce or prevent breakage while collapsing and/or to have an increased resilience. Alternatively or additionally, the straight elements of structure 204 can be joined together with a different material, for example some kind of gum, which is more flexible than the straight elements themselves. Optionally, the joints dissolve in the stomach (optionally after some time where satiety is induced or enhanced) allowing the constituting parts of the structure to pass out of the stomach.

Alternatively, structure 204 comprises an articulated structure, made, for example, from a bio-compatible metal, with joints that have a preferred state, due to springs for example, and which recovers its preferred state, thereby expanding in volume, when capsule 200 dissolves. Alternatively, structure 204 is made of a shape memory alloy or a pre-shaped gum or silicone, and expands to a memorized shape when capsule 200 dissolves.

It should be noted that, if structure 204 does not expand inside capsule 200 because of the forces of shell 202 confining it, then structure 204 may also not expand inside the esophagus, if shell 202 accidentally dissolves or breaks and releases structure 204 in the esophagus, instead of in the stomach. The walls of the esophagus will also exert forces on structure 204, preventing it from expanding. This is a potentially advantageous safety feature of capsule 200. Optionally, the material of the structure (e.g., the gum of the joints) will degrade in the esophagus, optionally releasing the constituents of the structure into the stomach.

Figure 2E:
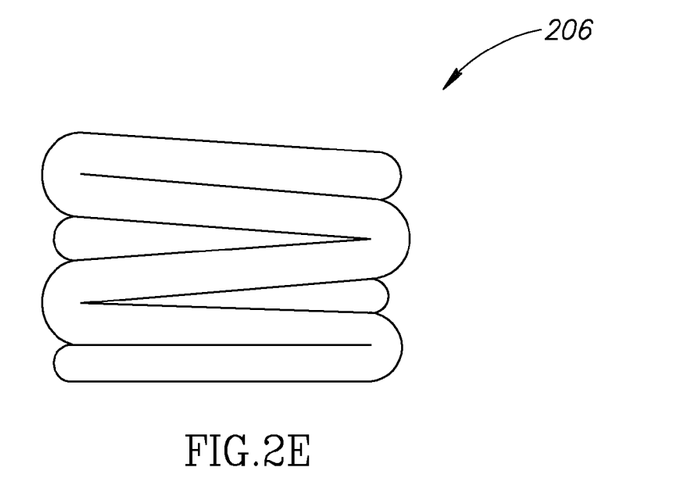
FIGS. 2E and 2F schematically show a sequence of perspective views of a compressed element expanding when it is released from a capsule, according to another exemplary embodiment of the invention.
Figure 2F:
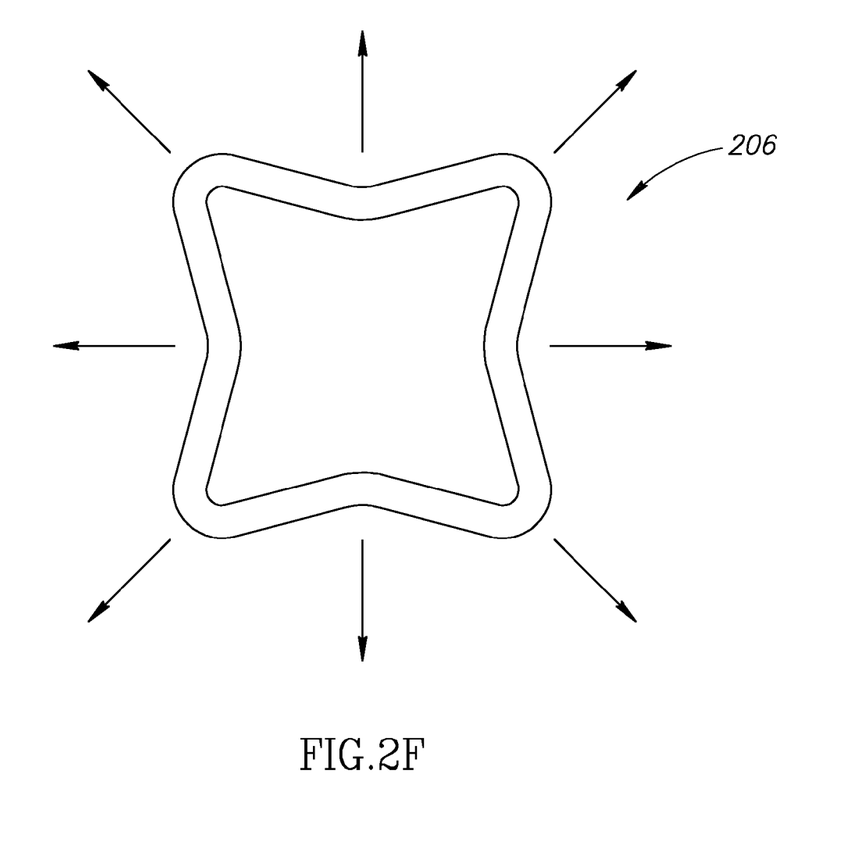

FIG. 2E shows an element 206, comprising eight segments that are folded up compactly. A number of such elements are optionally enclosed in capsule 200, where they remain compressed and folded up. When capsule 200 dissolves, each element 206, no longer compressed, expands to form a ring shape, as shown in FIG. 2F. When a number of such rings are stuck together, or lean together, at random angles, there will be a lot of empty space between them, giving the mass of elements 206 a much greater envelope volume than the volume of capsule 200.

Figure 3:
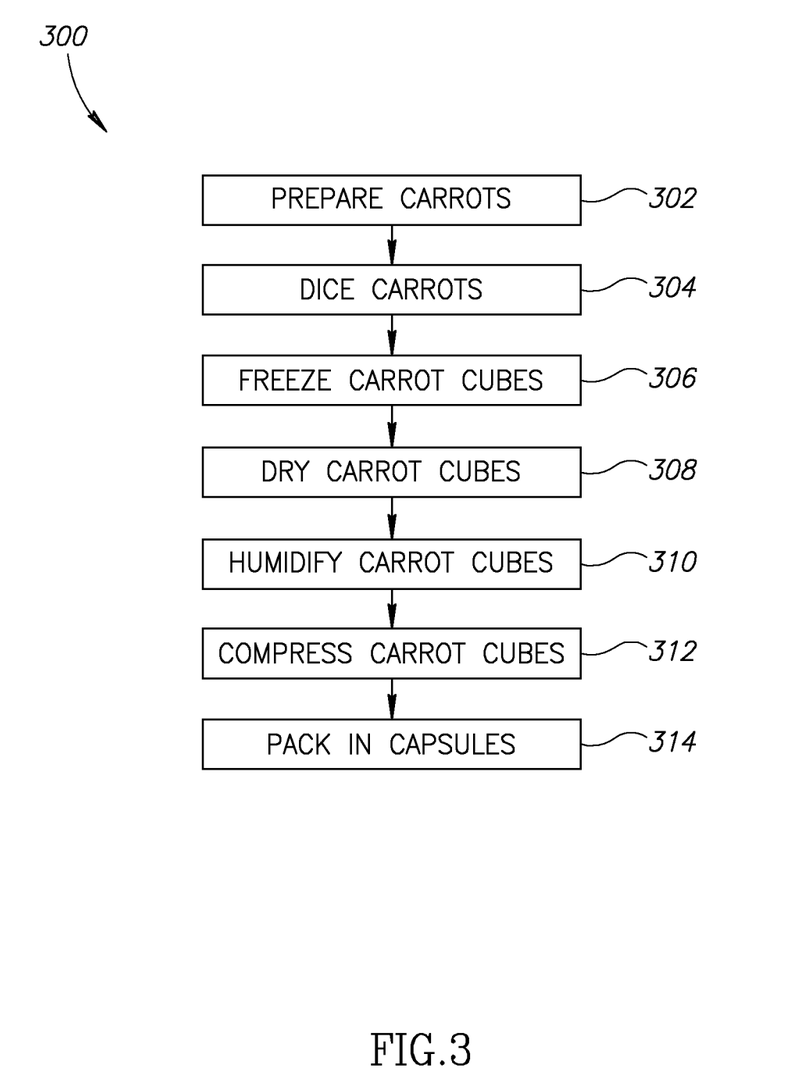
FIG. 3 is a flowchart of a manufacturing method for making compressible freeze-dried carrots, according to an exemplary embodiment of the invention.

FIG. 3 shows a flowchart 300 for a method of manufacturing a highly compressible freeze-dried food material, such as carrot, which expands by a large factor when it is released from compression, and expands by a further large factor when it absorbs water. The material is suitable to use for elements 104 in FIGS. 1A-1C, or for structure 204 in FIGS. 2A-2D. A similar method can be used for certain vegetables and fruits other than carrots, possibly with adjustments in some of the parameters, and the references to "carrot" in FIG. 3 are only exemplary. The manufacturing preferably takes place in certified food manufacturing facilities, under conditions of good manufacturing process.

At 302, the carrots are optionally prepared by washing, sorting, peeling, cutting, and blanching. Although blanching is optionally used to stop enzymatic activity and give the product a longer shelf life, the carrots are optionally not cooked for too long, since this tends to reduce their elasticity when they are freeze-dried and humidified. This is in contrast to dried carrots prepared for use in instant soups, which are generally cooked first.

At 304, the carrots are diced into small cubes, for example smaller than 10 mm on a side. Alternatively, other shapes are used instead of or in addition to cubes, and the reference to "cubes" in FIG. 3 is only exemplary. At 306, the carrots are frozen, and optionally kept at −18° C. for at least 24 hours. If sealed in a polyethylene bag, the frozen carrots can be stored at this temperature for up to 2.5 years.

At 308, the frozen carrot cubes are dried, by placing them on trays in a freeze dryer. The dryer is closed, and a high vacuum, for example less than 0.1 mbar, is applied, optionally for 2 hours. Drying is then initiated by circulating heating fluid, optionally at about 40° C., in the freeze dryer shelves, and optionally continued for about 24 hours, or until the water content is about 3% by weight. At this point, the carrot cubes have shrunk to about 80% or 90% of their original volume, with the original water largely replaced by small air pockets.

Figure 4:
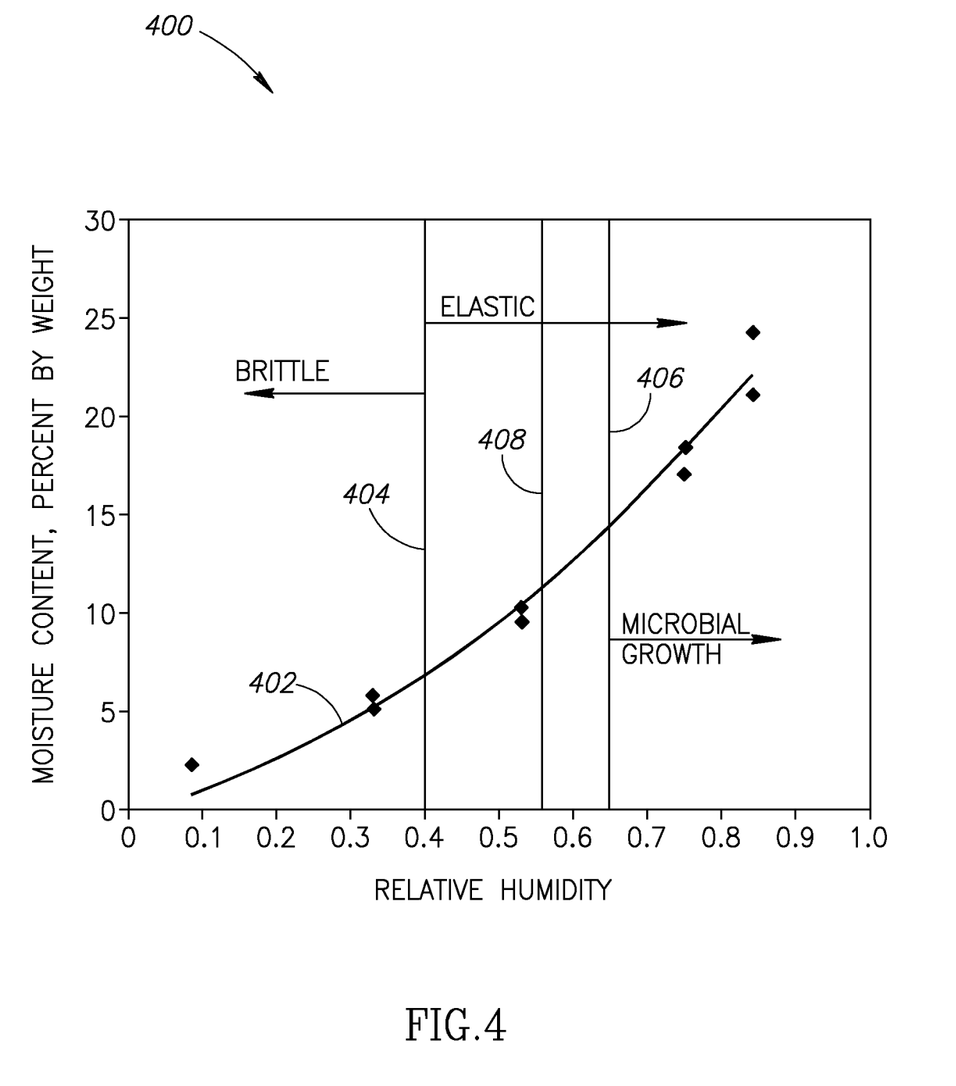
FIG. 4 is a plot of moisture content vs. relative humidity for the compressible freeze-dried carrots described in FIG. 3.

At such a low water content, the carrots tend to be brittle, and they are optionally humidified at 310, to restore some of their water content, making them more elastic. Alternatively, incomplete drying may be practiced. FIG. 4 shows a plot 400 of equilibrium moisture content vs. relative humidity for freeze-dried carrot cubes. Curve 402 is a fit to the experimental data points, shown as small diamonds. Generally, the carrots are found to be elastic if the water content is greater than 6%, and according to curve 402, this requires that the carrots be humidified at a relative humidity of greater than 40% (or water activity greater than 0.4), i.e. to the right of vertical line 404 in plot 400. The humidification process is optionally continued for 5 to 7 days. If the relative humidity is too high, however, microbes can grow on the carrot cubes. This occurs at a relative humidity of 63% (or water activity of 0.63) or greater, i.e. to the right of vertical line 406 in plot 400. Hence, the humidification should preferably occur in the regime between lines 404 and 406. Optionally, to make sure that the humidity does not get too high, the humidification process takes place at a nominal relative humidity of no more than 55%. Since the carrots become more elastic, and more compressible, the higher the relative humidity is, the optimal humidity to use is about 55%, i.e. at line 408 in plot 400. This corresponds to a water content of 10% by weight for the carrot cubes after they have been humidified. In general, if the humidification takes place between 40% and 55% relative humidity, the water content will be between 6% and 10%. The carrot cubes are now highly compressible, because much of their volume consists of small air pockets, and they are elastic enough to compress without breaking, so the compressibility is fully or largely reversible. The optimal water content values may vary between batches and varieties of a same source material (such as carrots) or for different materials (such as kohlrabi).

At 312, the carrot cubes are compressed to about 10% of their volume before drying, and at 314, the compressed carrot cubes are put inside gelatin capsules. Up to 20 compressed cubes of this size can be fit into a 00 size gelatin capsule. Optionally, one or more chemicals is added to the capsule as well, for example sticking agents to make the cubes stick together, thickening agents, and/or drugs to aid in weight loss, for example as described above.

The invention has been described in the context of the best mode for carrying it out. It should be understood that not all features shown in the drawing or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to."

The invention claimed is:

1. A capsule for suppressing appetite, comprising:
   a) a shell which dissolves in the stomach; and
   b) at least one folded mechanical structure formed from natural vegetable pieces, wherein said at least one folded mechanical structure comprises:
   a plurality of elements, and
   a plurality of joints joining ends of said plurality of elements to define a plurality of voids between said plurality of elements,
   wherein a natural fibrous structure of said natural vegetable pieces is preserved through a processing of said at least one folded mechanical structure, said processing comprising:
   freeze drying,
   folding thereby collapsing said plurality of voids, and packing said at least one folded mechanical structure into said shell, wherein said plurality of elements and said plurality of joints expand inside the stomach; after said shell dissolves to regain at least some of their original shape and unfold said compressed at least one folded mechanical structure redefining said plurality of voids.

2. A capsule according to claim 1, wherein the elements expand inside the stomach, after the shell dissolves, to form a mass with an expanded volume at least 3 times the volume of the capsule.

3. A capsule according to claim 2, wherein the expanded volume is at least 5 times the volume of the capsule.

4. A capsule according to claim 3, wherein the expanded volume is at least 10 times the volume of the capsule.

5. A capsule according to claim 1, wherein the elements consist of material substantially all of which leaves the stomach of a normal person in less than 12 hours.

6. A capsule according to claim 5, wherein substantially all of the material leaves the stomach in less than 9 hours.

7. A capsule according to claim 6, wherein substantially all of the material leaves the stomach in less than 6 hours.

8. A capsule according to claim 1, wherein the elements individually expand when they absorb fluid inside the stomach.

9. A capsule according to claim 1, wherein the elements comprise a food material approved for human consumption.

10. A capsule according to claim 9, wherein the food material comprises a freeze-dried vegetable.

11. A capsule according to claim 10, wherein the material comprises between 6% and 10% water by weight.

12. A capsule according to claim 1, wherein the elements comprise an inert non-food material.

13. A capsule according to claim 1, wherein said at least one folded mechanical structure is in a collapsed state when it is inside the shell, and which unfolds to a less collapsed state when it is released from the shell.

14. A capsule according to claim 13, wherein the expansion of said at least one folded mechanical structure is due at least partly to the removal of constraining forces exerted on said at least one folded mechanical structure by the shell.

15. A capsule according to claim 13, wherein the expansion of said at least one folded mechanical structure is at least partly triggered by exposure to water.

16. A capsule according to claim 15, wherein the expansion of said at least one folded mechanical structure is due at least partly to the absorption of fluid, which makes said at least one folded mechanical structure more rigid.

17. A capsule according to claim 15, wherein the expansion of said at least one folded mechanical structure is due at least partly to the absorption of fluid which makes the individual elements unfold.

18. A capsule according to claim 13, wherein said at least one folded mechanical structure corresponds to an array of polyhedrons; with each element corresponding to an edge of one or more of the polyhedrons.

19. A method of inducing satiety in a patient, comprising feeding the patient one or more capsules according to claim 1.

20. A method of manufacturing capsules of expandable material for inducing satiety, comprising:
a) freeze-drying at least one folded mechanical structure formed from edible vegetable pieces comprising a fibrous structure to a moisture content less than 5%;
b) humidifying said at least one folded mechanical structure to a water content of at least 6% by weight, thereby making said at least one folded mechanical structure elastic;
c) folding said at least one folded mechanical structure; and
d) putting said at least one folded mechanical structure into a shell of a capsule small enough to swallow;
wherein the shell is configured to dissolve in the stomach, and said at least one folded mechanical structure is configured to unfold in the stomach sufficiently to suppress or reduce appetite, and wherein said at least one folded mechanical structure inside has shell has a preserved said fibrous structure.

21. A method according to claim 20, also including forming the vegetable pieces into shapes.

22. A capsule according to claim 1, wherein the elements retain enough of said fibrous structure so that they are elastic at least when they absorb fluid inside the stomach after the shell dissolves.

23. A capsule according to claim 22, wherein the elements retain enough of said fibrous structure so that they are elastic when they are inside the shell.

24. A capsule according to claim 4, wherein the expanded volume is at least 20 times the volume of the capsule.

25. A capsule according to claim 1, wherein the elements retain enough of their mechanical structure so that the elements themselves expand by a factor of 4 in volume, when they absorb fluid in the stomach after the shell dissolves.

26. A capsule according to claim 1, wherein the elements themselves expand to at least 70% of the original volume of the vegetable pieces, when they absorb fluid in the stomach after the shell dissolves.

27. A capsule according to claim 1, wherein the elements are each at least about 0.5 mm in diameter when they are inside the shell.

28. A capsule according to claim 15, wherein the expansion of said at least one folded mechanical structure is due at least partly to the absorption of fluid, which makes said at least one folded mechanical structure more elastic.

29. A capsule according to claim 1, wherein the vegetable pieces comprise pieces of fruit.

30. A capsule according to claim 1, wherein said fibrous structure retains its elasticity when its water content is reduced to 10% by weight.

31. A capsule according to claim 1, wherein the vegetable pieces comprise digestible material.

32. A capsule for suppressing appetite, comprising:
a) a shell which dissolves in the stomach; and
b) at least one folded mechanical structure inside said shell formed from natural vegetable pieces, wherein said at least one folded mechanical structure comprises a plurality of elements that define a plurality of voids between said plurality of elements formed by removing material from a block of natural vegetable material, wherein said natural vegetable pieces are dehydrated and preserve an original fibrous structure of said natural vegetable pieces.

33. A capsule according to claim 1, wherein at least some of said voids are between said natural vegetable pieces.

34. A capsule according to claim 1, wherein at least some of said voids are within said natural vegetable pieces.

* * * * *